United States Patent
Levitan

(10) Patent No.: US 9,393,374 B2
(45) Date of Patent: Jul. 19, 2016

(54) INTRODUCER FOR SURGICAL AIRWAY CATHETERS

(71) Applicant: Richard M. Levitan, Rednor, PA (US)

(72) Inventor: Richard M. Levitan, Rednor, PA (US)

(*) Notice: Subject to any disclaimer, the term of this patent is extended or adjusted under 35 U.S.C. 154(b) by 234 days.

(21) Appl. No.: 14/198,650

(22) Filed: Mar. 6, 2014

(65) Prior Publication Data
US 2014/0283821 A1    Sep. 25, 2014

Related U.S. Application Data

(60) Provisional application No. 61/804,801, filed on Mar. 25, 2013.

(51) Int. Cl.
*A61M 16/00* (2006.01)
*A61M 16/04* (2006.01)

(52) U.S. Cl.
CPC ....... *A61M 16/0488* (2013.01); *A61M 16/0472* (2013.01)

(58) Field of Classification Search
CPC .............. A61M 16/0488; A61M 16/0472; A61M 29/00; A61M 25/0152; A61M 25/0138; A61M 25/0054; A61M 16/0465; A61M 16/0495; A61M 16/0497; A61M 25/0016; A61M 25/0102
See application file for complete search history.

(56) References Cited

U.S. PATENT DOCUMENTS

| | | | |
|---|---|---|---|
| 2,705,959 A * | 4/1955 | Elmore | A61B 1/267 128/207.14 |
| 2,865,374 A | 12/1958 | Brown et al. | |
| 2,991,787 A | 7/1961 | Shelden et al. | |
| 3,334,631 A | 8/1967 | Stebleton | |
| 3,556,103 A | 1/1971 | Calhoun et al. | |
| 3,957,055 A | 5/1976 | Linder et al. | |
| 3,968,800 A | 7/1976 | Vilasi | |
| 4,246,897 A | 1/1981 | Muto | |
| 5,186,168 A | 2/1993 | Spofford et al. | |

(Continued)

FOREIGN PATENT DOCUMENTS

| | | |
|---|---|---|
| WO | WO2006087512 A1 | 8/2006 |
| WO | WO2008034872 A1 | 3/2008 |
| WO | WO2009156909 A1 | 12/2009 |

OTHER PUBLICATIONS

International Search Report and Written Opinion; Mailed Aug. 18, 2014 for the PCT Application No. PCT/US2014/031667.

(Continued)

*Primary Examiner* — Bradley Philips
(74) *Attorney, Agent, or Firm* — Mendelsohn Dunleavy, P.C.; Steve Mendelsohn

(57) ABSTRACT

In one embodiment, an introducer has a round handle; a first curved, flattened (i.e., oval) section connected to the handle; a first straight, unflattened (i.e., circular) section connected to the first curved section; a second curved, flattened section connected to the first straight section; and a last straight, unflattened section connected to the second curved section. The curved, flattened sections allow the introducer to unbend in the anterior-posterior direction to enable a user to introduce a tube or other airway catheter into a surgical airway. The major axis of the oval sections is equal to the diameter of the circular sections, substantially preventing side-to-side bending of the introducer. A rounded distal end provides tactile feedback resulting from palpation of the patient's anterior tracheal rings to confirm proper insertion of the introducer, while tenting of the skin indicates improper insertion.

12 Claims, 3 Drawing Sheets

(56) References Cited

U.S. PATENT DOCUMENTS

| | | | |
|---|---|---|---|
| 5,217,005 | A | 6/1993 | Weinstein |
| 5,279,285 | A | 1/1994 | Griggs |
| 5,429,127 | A | 7/1995 | Kolobow |
| 5,507,279 | A | 4/1996 | Fortune et al. |
| 5,546,936 | A | 8/1996 | Virag et al. |
| 5,546,937 | A | 8/1996 | Stuart et al. |
| 5,658,263 | A * | 8/1997 | Dang ................ A61M 25/0041 604/264 |
| 5,928,198 | A | 7/1999 | Lester |
| RE36,611 | E | 3/2000 | French |
| 6,481,436 | B1 | 11/2002 | Neame |
| 6,637,435 | B2 | 10/2003 | Ciaglia et al. |
| 2005/0279363 | A1 | 12/2005 | Cruz |
| 2006/0124134 | A1 | 6/2006 | Wood |
| 2008/0017195 | A1 | 1/2008 | Yoshida |
| 2008/0257359 | A1 | 10/2008 | Rumsey |
| 2008/0275391 | A1 | 11/2008 | Lyons et al. |
| 2009/0050146 | A1 | 2/2009 | Smith |
| 2010/0012130 | A1 | 1/2010 | Guerra |
| 2010/0108060 | A1 | 5/2010 | Pecherer et al. |
| 2011/0313402 | A1 * | 12/2011 | Morero ............. A61M 25/0041 604/528 |

OTHER PUBLICATIONS

Paladino, L., et al., "Development of a Rapid, Safe, Fiber-Optic Guided, Single-Incision Cricothyrotomy Using a Large Ovine Model: A Pilot Study", Resuscitation, Elsevier, IE, vol. 80, No. 9, Sep. 1, 2009, pp. 1066-1069, XP026460486.

* cited by examiner

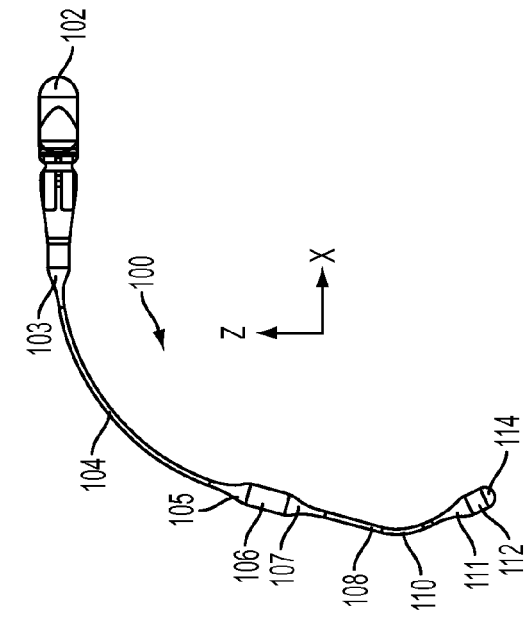
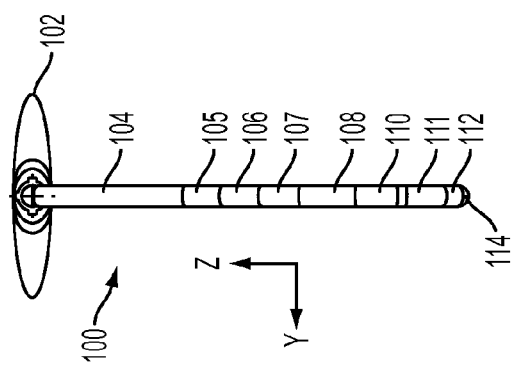
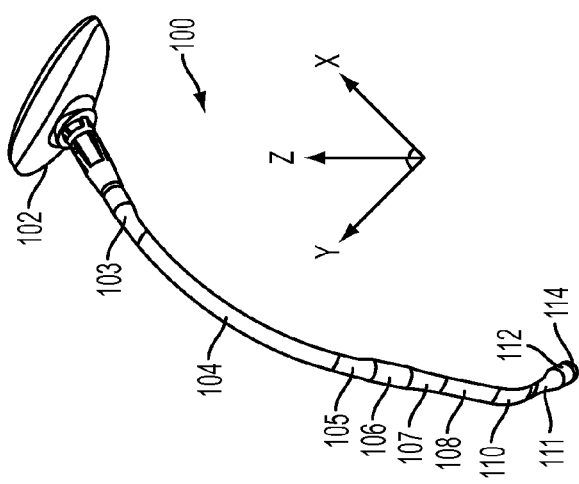

INTRODUCER FOR SURGICAL AIRWAY CATHETERS

CROSS-REFERENCE TO RELATED APPLICATIONS

This application claims the benefit of the filing date of U.S. provisional application No. 61/804,801, filed on Mar. 25, 2013, the teachings of which are incorporated herein by reference in their entirety.

The subject matter of this application is related to the subject matter of U.S. patent application Ser. Nos. 13/484,933 and 13/501,602, the teachings of both of which are incorporated herein by reference in their entirety.

BACKGROUND

1. Field of the Invention

The present disclosure relates to medical devices and techniques for using medical devices and, more specifically but not exclusively, to an introducer for surgical airway catheters.

2. Description of the Related Art

This section introduces aspects that may help facilitate a better understanding of the invention. Accordingly, the statements of this section are to be read in this light and are not to be understood as admissions about what is prior art or what is not prior art.

Emergency cricothyrotomy or tracheotomy can be performed using a traditional open technique (scalpel and tracheal hook), trochar type devices, or with a wire guided percutaneous approach using dilators (a.k.a. Seldinger technique). The preferred emergency surgical airway insertion site is the cricothyroid membrane because it is a relatively large space, it is devoid of large blood vessels, and it is generally accessible regardless of body habitus.

Open techniques involve a skin incision, stabilization of the trachea with either a tracheal hook or other instrument, and subsequent placement of a tracheal tube or surgical airway tube (tracheostomy tube or other short airway catheter) directly into the opening. These techniques are intimidating to providers without formal surgical training. Open techniques require fine motor control under situations of marked duress for operators and extreme time constraints for patients. Examples of these situations include hostile battlefield and tactical situations, in addition to traumatic presentations to emergency departments. Risks include vascular injury of laterally adjacent structures, perforation of the posterior trachea, creation of false subcutaneous passages, and fractures of the thyroid or cricoid cartilages due to the tracheal hook. Open surgical techniques are also technically challenging due to variations in the thickness of anterior neck tissues and bleeding that obscures landmarks. If control of the trachea by the tracheal hook is lost during the procedure, the opening may retract and be difficult to re identify.

Trochar type devices use sharp pointed blunt or hollow points to enter the skin and puncture the trachea, after which an airway tube is inserted (either over or through the sharp trochar). Upon insertion, the direction of force is in an anterior to posterior direction. This can cause compression of the trachea (decreasing the anterior posterior dimension) due to sudden and forceful entry into the trachea. The sharp point of such a device may then puncture the thin wall of the posterior trachea. This can result in procedural failure, false passage, mediastinal injury, subcutaneous emphysema, and tension pneumothorax. If the insertion point is off midline, then the great vessels of the neck (carotid artery and jugular vein) may be disrupted resulting in major bleeding. In many clinical situations that require surgical airway access, there is injury to the neck that may distort landmarks and proper identification of midline may be difficult.

Wire guided percutaneous devices are less intimidating to providers since a needle is used to place a wire into the trachea and no direct skin or tracheal incision is required. A skin or tissue plug in the needle may make identification of the trachea with a needle difficult or impossible. It is also possible to create a false passage with the wire. After the wire is placed, a dilator is used to serve as a stent for a cuffed short airway tube. To pass the dilator, the skin incision must be enlarged. Passage of the dilator and tube involves a relative sharp turn into the trachea. Expanding the skin incision requires cutting down on the wire using fine motor control of the scalpel while holding the wire in place. An inadequate skin incision, or an inappropriate insertion angle of the dilator and tube, may make passage into the trachea mechanically difficult. It can be difficult to control both dilator and tube during forceful insertion over the wire. The percutaneous method requires an average of 100 seconds before the patient can be ventilated. Since there is great reluctance for operators to initiate surgical airways, an additional 100 second delay to ventilation may result in hypoxic injury or death.

BRIEF DESCRIPTION OF THE DRAWINGS

Other embodiments of the invention will become more fully apparent from the following detailed description, the appended claims, and the accompanying drawings in which like reference numerals identify similar or identical elements.

FIGS. 1(A)-1(D) show four different views of an introducer according to one embodiment of the present disclosure;

DETAILED DESCRIPTION

Figure 2:
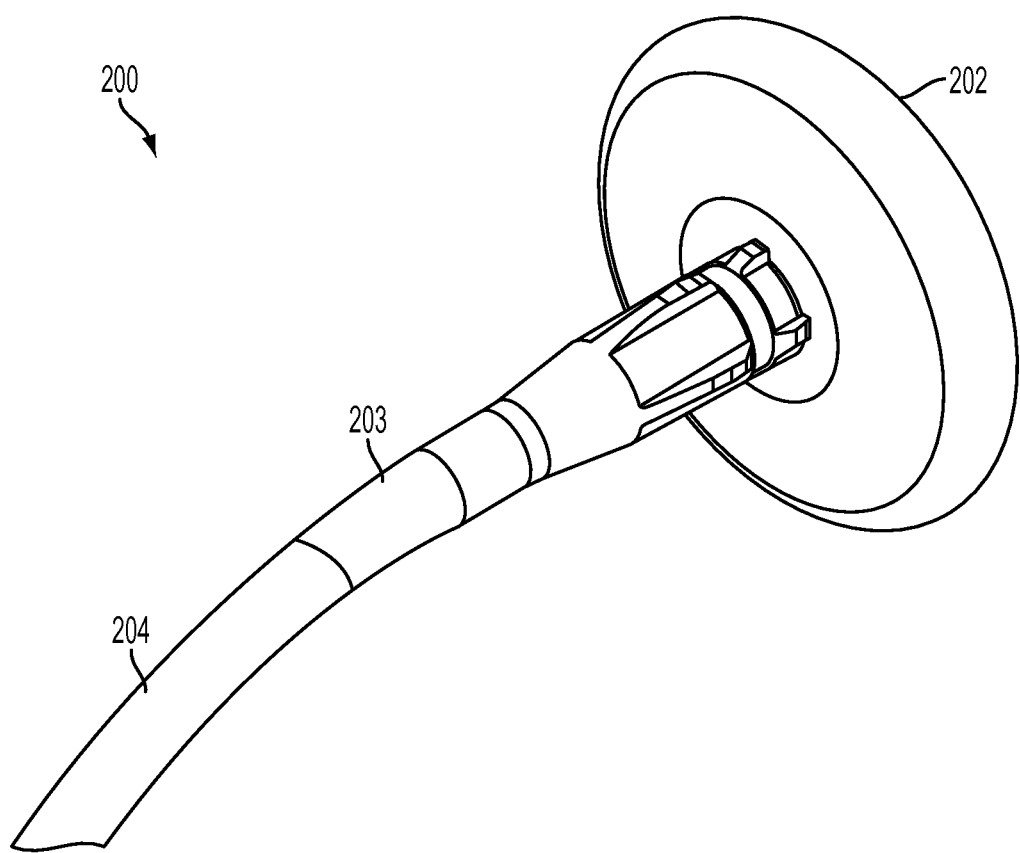
FIG. 2 shows a perspective view of a portion of an introducer according to another embodiment of the present disclosure.

A published article by Paladino, DuCanto, and Manoach describes use of a rigid optical stylet for stabilizing the trachea after neck incision, followed by direct visualization of the trachea through the fiberoptic instrument. See "Development of a rapid, safe, fiber-optic guided, single-incision cricothyrotomy using a large ovine model: a pilot study," Paladino L., DuCanto J., and Manoach S., Resuscitation, 2009 September; 80 (9):1066-9 (Epub 2009 Jul. 15). After the opening is expanded with another scalpel incision, the authors passed a pre-loaded, snug-fitting short airway tube over the stylet into the trachea.

Problems in the prior art are addressed in accordance with the principles of the present disclosure by providing technique for inserting a surgical airway catheter using an introducer that is simpler than the device described by Paladino et al. and without the need for fiberoptic guidance.

FIGS. 1(A)-1(D) show four different views of introducer 100 according to one embodiment of the present disclosure. In particular, FIG. 1(A) shows a perspective view while FIGS. 1(B)-(D) show three difference side views from directions parallel to the X, Y, and Z axes, respectively. As shown in the figures, introducer 100 has:

a flared or elongated (e.g., oval), proximal handle 102;

a first curved section 104 having a flattened (e.g., oval) cross section and connected to the handle via an (e.g., circular-to-oval) transition section 103;

a first straight section 106 having an unflattened (e.g., circular) cross section and connected to the first curved section 104 via an (e.g., oval-to-circular) transition section 105;

a second straight section 108 having a flattened (e.g., oval) cross section and connected to the first straight section 106 via an (e.g., circular-to-oval) transition section 107;

a second curved section 110 having a flattened (e.g., oval) cross section and connected directly to the second straight section 108;

a third and last straight section 112 having an unflattened (e.g., circular) cross section and connected to the second curved section 110 via an (e.g., oval-to-circular) transition section 111, and a rounded (e.g., hemispherical) tip 114 connected directly to the last straight section 112 to form a distal end of the introducer 100.

As evident in FIGS. 1(C) and 1(D), all nine sections 103-112 have the same width, while the three flattened sections 104, 108, and 110 are thinner than the two unflattened sections 106 and 112. In one implementation, the two unflattened sections 106 and 112 have circular cross sections, while the three flattened sections 104, 108, and 110 have oval cross sections, where the major axis of the oval cross sections of the three flattened sections is equal to the diameter of the circular cross sections of the two unflattened sections.

The asymmetry of the three flattened sections results in those sections enabling introducer 100 to bend more easily within the XZ plane of FIG. 1(C) than in either the ZY plane of FIG. 1(B) or the XY plane of FIG. 1(D). As described further below, this asymmetric flexibility assists in inserting introducer 100 into a patient's trachea through an opening in the patient's neck.

As viewed in FIG. 1(C), the first curved section 104 curves down approximately 80 degrees from handle 102 to the first straight section 106, while the second curved section 110 curves in the same direction by another approximately 30 degrees from the second straight section 108 to the last straight section 112. As described further below, this bending assists in inserting introducer 100 into a patient's trachea through an opening in the patient's neck.

Introducer 100 combines a J-shaped short curvilinear introducer with certain mechanical properties that permit palpation of the anterior tracheal rings along with ease of insertion into the trachea. The device combines a deliberately short introducer which can be inserted under the patient's mandible, into a percutaneous hole in the airway (at the cricothyroid membrane or into the trachea). The J-shape permits this and allows upward tension on the anterior trachea. If the introducer were straight, it would have trouble being inserted beneath the mandible and contacting the anterior trachea. In many emergency situations, the patient's head cannot be extended. By hooking the trachea (pulling upward) and then moving the introducer in and out, the anterior tracheal rings are consistently appreciated. Because the device has a certain spring to it—created by the durometer of the material and a partially thinned out section—the rings are easily and reliably appreciated via tactile feedback. This is without aspiration of air, and independent of blood or vomitus. Accordingly, the device confirms entering the trachea in emergency and battlefield conditions (where blood and vomitus are the rule).

The mechanical properties of the introducer, having a thinner anterior-posterior (AP) diameter and a full side-to-side dimension that matches the rounded sections proximally and distally, gives a sensitive feel for tracheal rings as it is moved up and down (along with its curvature that brings tip upward for easy contact). Secondly, since it is more flexible in anterior/posterior movement, it can also unbend upon full insertion into the trachea. The trachea is an essentially straight tube that descends posteriorly into the thorax. A rigid curvilinear rod would not do this and could either potentially injure the trachea or prevent full insertion.

The introducer may be made of a smooth material, perhaps with lubricious properties, and a smooth transition between each thinned section to each fully round section, in order to ensure easy movement of the pre-loaded airway tube off the introducer. The overall length of the introducer (between about 12 and about 16 centimeters) is designed to permit palpation of the trachea between the incision at the cricothyroid membrane and before the tracheal bifurcation (a distance in adults of only about 11 centimeters). The introducer projects between about 2 and about 8 centimeters beyond the end of the airway tube. This length also permits pre-loading of a short airway tube with enough length to palpate the trachea. Once palpated, the introducer and pre-loaded tube can be simultaneously inserted into the trachea. The flexibility of the introducer permits full insertion of both devices as a unit, and the overall length does not project too long to reach narrowing areas of the tracheal tree.

The thinned sections of the introducer still has a full side-to-side dimension, which provides side-to-side rigidity of the introducer, which can permit widening of the surgical incision (by side-to-side movement) if needed.

FIG. 2 shows a perspective view of a portion of an introducer 200 according to another embodiment of the present disclosure. Introducer 200 is identical to introducer 100 of FIG. 1, except that introducer 200 has a round handle 202 as compared to the elongated handle 102 of introducer 100.

Figure 4:
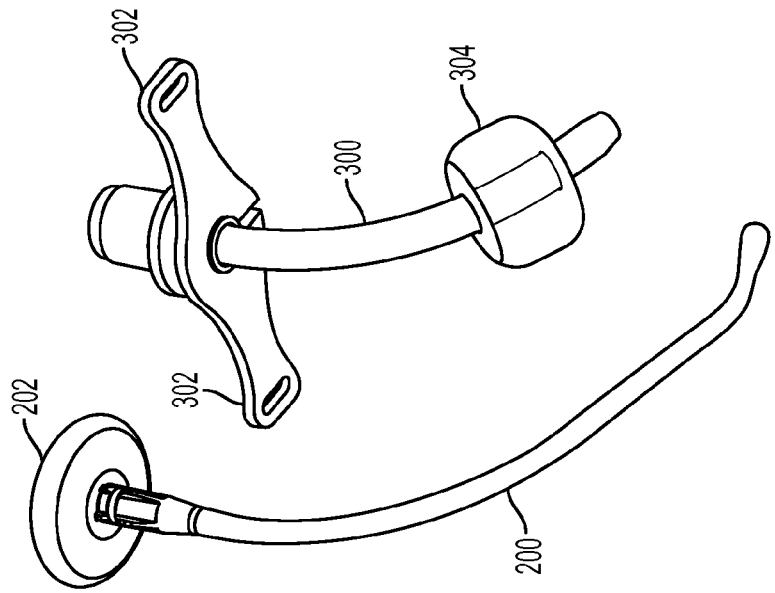
FIG. 4 shows separate, perspective views of the introducer and the tube of FIG. 3.
Figure 3:
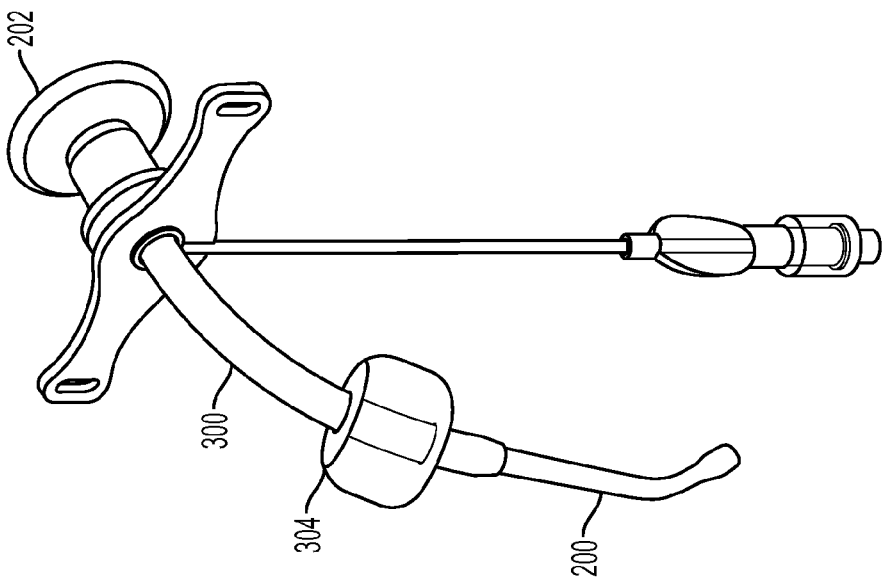
FIG. 3 shows a perspective view of the introducer of FIG. 2 loaded with an overlying silicone, short, cuffed tube.

FIG. 3 shows a perspective view of introducer 200 of FIG. 2 loaded with an overlying silicone, short, cuffed tube 300. [Rich, what is the thing hanging down in FIG. 3?] FIG. 4 shows separate, perspective views of introducer 200 and tube 300.

The introducer's overall rigidity allows for lifting (on insertion) to maintain contact with the anterior trachea (i.e., verification of tracheal placement by palpation of the rings), but its flexibility allows for "unbending" and full insertion. Conversely, if the device is placed subcutaneously, then lifting causes tenting of the skin (and no tactile sensation of the tip bouncing over the rings).

The length of the device is short enough that it will not go past the carina in most adults but is long enough (beyond the overlying airway tube) to permit tactile palpation of the trachea (with lifting). The overall size and weight (including the cuffed tube) make it a much smaller (and lighter) package than a standard trachea tube and bougie. It is small enough to be carried in a pocket or belt pouch.

After insertion, the introducer 200 is withdrawn by grabbing the proximal handle 202 of the device. The tube 300 can be secured through two tabs 302 alongside its proximal 15-mm connector (using, e.g., umbilical tape) or with a supplied neck strap (for use with gloves, mittens, etc.). The tube itself has a thin profile and tear-resistant cuff 304 and is flexible to facilitate sliding off the introducer, but it may have wire reinforcement (not shown) to prevent kinking.

Although the disclosure has been described in the context of an introducer having a last straight section 112 having an unflattened (e.g., circular) cross section, in alternative embodiments, the last straight section has a flattened (e.g., oval) cross section.

Unless explicitly stated otherwise, each numerical value and range should be interpreted as being approximate as if the word "about" or "approximately" preceded the value or range.

It will be further understood that various changes in the details, materials, and arrangements of the parts which have been described and illustrated in order to explain embodiments of this invention may be made by those skilled in the art without departing from embodiments of the invention encompassed by the following claims.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. An introducer for surgical airway catheters, the introducer comprising:
   a handle;
   a first curved section having a flattened cross section and connected to the handle;
   a first straight section having an unflattened cross section and connected to the first curved section;
   a second curved section having a flattened cross section and connected to the first straight section;
   a last straight section connected to the second curved section and forming a distal end of the introducer, wherein;
   the first curved section is connected to the handle via a first transition section;
   the first straight section is connected to the first curved section via a second transition section;
   the second curved section is connected to the first straight section via a third transition section; and
   the last straight section is connected to the second curved section via a fourth transition section;
   wherein the first and second curved sections each form a radius of curvature and the introducer includes an anteriorly located surface and a posteriorly located surface, and the first curved section radius of curvature locates on the same anteriorly located surface as the second curved section radius of curvature.

2. The introducer of claim 1, wherein the last straight section has an unflattened cross section.

3. The introducer of claim 1, wherein:
   the first curved section curves by about 80 degrees from the handle to the first straight section; and
   the second curved section curves by about 30 degrees from the first straight section to the last straight section.

4. The introducer of claim 1, wherein:
   the first and second curved sections have oval cross sections; and
   the first and last straight sections have circular cross sections.

5. The introducer of claim 4, wherein a major axis of the oval cross sections of the first and msecond curved sections is equal to a diameter of the circular cross sections of the first and last straight sections.

6. The introducer of claim 1, further comprising a second straight section having a flattened cross section and connected between the first straight section and the second curved section.

7. The introducer of claim 1, wherein the last straight section has a rounded tip.

8. The introducer of claim 1, wherein:
   the second transition section transitions between the unflattened cross section of the first straight section and the flattened cross section of the first curved section;
   the third transition section transitions between the flattened cross section of the second curved section and the unflattened cross section the first straight section; and
   the fourth transition section transition between an unflattened cross section of the last straight section and the flattened cross section of the second curved section.

9. The introducer of claim 1, wherein:
   the first and second curved sections are curved in an anterior-posterior direction; and
   the flattened cross section of the first and second curved sections enable the introducer to bend easier in the anterior-posterior direction than in a side-to-side direction.

10. The introducer of claim 1, wherein the introducer is loadable with a tube such that the loaded introducer is usable to introduce the tube into a surgical airway.

11. The introducer of claim 1, wherein:
    the first and second curved sections have oval cross sections;
    the first and last straight sections have circular cross sections;
    a major axis of the oval cross sections of the first and second curved sections is equal to a diameter of the circular cross sections of the first and last straight sections;
    further comprising a second straight section having a flattened cross section and connected between the first straight section and the second curved section;
    the last straight section has a rounded tip;
    the second transition section transition between the unflattened cross section of the first straight section and the flattened cross section of the first curved section;
    the third transition section transition between the flattened cross section of the second straight section and the unflattened cross section of the first curved section;
    the second curved section is connected directly to the second straight section;
    the fourth transition section transitions between an unflattened cross section of the last straight section and the flattened cross section of the second curved section;
    the first and second curved sections are curved in an anterior-posterior direction;
    the flattened cross section of the first and second curved sections enable the introducer to bend easier in the anterior-posterior direction than in a side-to-side direction; and
    the introducer is loadable with a tube such that the loaded introducer is usable to introduce the tube into a surgical airway.

12. The introducer of claim 11, wherein:
    the first curved section curves by about 80 degrees from the handle to the first straight section; and the second curved section curves by about 30 degrees from the second straight section to the last straight section.

* * * * *